US010515718B2

(12) United States Patent
Delgrande et al.

(10) Patent No.: US 10,515,718 B2
(45) Date of Patent: *Dec. 24, 2019

(54) POINT-OF-CARE TESTING SYSTEM

(71) Applicant: Roche Diagnostics Operations, Inc., Indianapolis, IN (US)

(72) Inventors: Diego Delgrande, Lucerne (CH); Gillian Hall, Baar (CH); Alejandro Morcillo Montejo, Lloret de Mar (ES); Stephanie Shufelt, Rotkreuz (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/018,473

(22) Filed: Jun. 26, 2018

(65) Prior Publication Data

US 2018/0301207 A1 Oct. 18, 2018

Related U.S. Application Data

(63) Continuation of application No. 15/140,542, filed on Apr. 28, 2016, now Pat. No. 10,078,730.

(30) Foreign Application Priority Data

May 2, 2015 (EP) ..................... 15166151

(51) Int. Cl.
*H04L 29/06* (2006.01)
*G16H 10/60* (2018.01)
(Continued)

(52) U.S. Cl.
CPC ............. *G16H 10/60* (2018.01); *G16H 10/40* (2018.01); *G16H 40/40* (2018.01); *G16H 40/63* (2018.01);
(Continued)

(58) Field of Classification Search
CPC ................................ H04L 67/12; H04L 41/08
See application file for complete search history.

(56) References Cited

U.S. PATENT DOCUMENTS 6,386,882 B1 5/2002 Linberg
8,214,494 B1 7/2012 Slavin
(Continued)

FOREIGN PATENT DOCUMENTS

JP 2014-120173 A 6/2014
WO 2009/152140 A1 12/2009
(Continued)

OTHER PUBLICATIONS

Kim, Tiffany Hyun-Jin et al., Access Right Assignment Mechanisms for Secure Home Networks, Journal of Communications and Networks, 2011, pp. 175-186, vol. 13, No. 2.
(Continued)

*Primary Examiner* — Adnan M Mirza
(74) *Attorney, Agent, or Firm* — Roche Diagnostics Operations, Inc.

(57) ABSTRACT

A point of care (POC) testing system and a method for configuration of a POC testing system are disclosed that provide a workflow solution for the configuration management of POC analyzers. The POC system and method provide for convenient assisted workflows that enable efficient replacement of POC analyzers and enable traceable relocation of POC analyzers within, for example, a hospital.

20 Claims, 12 Drawing Sheets

(51) Int. Cl.
*H04L 29/08* (2006.01)
*H04B 1/3827* (2015.01)
*H04L 12/24* (2006.01)
*G16H 40/40* (2018.01)
*G16H 10/40* (2018.01)
*G16H 40/63* (2018.01)

(52) U.S. Cl.
CPC .......... *H04B 1/3827* (2013.01); *H04L 41/08* (2013.01); *H04L 67/12* (2013.01)

(56) References Cited

U.S. PATENT DOCUMENTS

| | | |
|---|---|---|
| 2005/0253722 A1 | 11/2005 | Droms et al. |
| 2006/0206389 A1 | 9/2006 | Elssner et al. |
| 2012/0011253 A1 | 1/2012 | Friedman et al. |
| 2012/0232367 A1 | 9/2012 | Allegri et al. |
| 2012/0233679 A1 | 9/2012 | Shedrinsky |
| 2013/0302770 A1 | 11/2013 | Miller |
| 2014/0117089 A1 | 5/2014 | Steimle et al. |
| 2014/0278832 A1 | 9/2014 | Glavina et al. |
| 2014/0282181 A1 | 9/2014 | Declerck |

FOREIGN PATENT DOCUMENTS

| | | |
|---|---|---|
| WO | 2011/017608 A1 | 2/2011 |
| WO | 2012/148564 A1 | 11/2012 |
| WO | 2013/085884 A1 | 6/2013 |

OTHER PUBLICATIONS

RadiometerMedical, Aquire open, smart, integrated point-of-care management, https://www.youtube.com/watch?v=ut16rY5iW5s#7=195, retrieved on Oct. 23, 2015, 1 page.

POINT-OF-CARE TESTING SYSTEM

CROSS-REFERENCE TO RELATED APPLICATIONS

This application is a continuation of U.S. application Ser. No. 15/140,542 filed Apr. 28, 2016, and claims priority to EP 15166151.9, filed May 2, 2015, which is hereby incorporated by reference.

BACKGROUND

The present disclosure generally relates to a point of care testing system and a method for configuration of a point of care testing system.

In vitro diagnostic testing has a major effect on clinical decisions, providing physicians with pivotal information. Particularly there is great emphasis on providing quick and accurate test results in critical care settings.

One field of diagnostic testing is conducted with large analytical instruments in laboratories. These instruments are operated by operators that are educated to maintain and operate such instruments.

Another field of diagnostic testing is bedside testing, or point of care testing (POCT). This type of diagnostic testing is performed mainly by nurses or medical staff primarily trained to operate the instruments available at the site of patient care, such as hospitals, emergency departments, intensive care units, primary care setting, medical centers, patient homes, a physician's office, a pharmacy or a site of an emergency.

Often, POCT needs to meet clinical and laboratory requirements for short turnaround times in critical care. Rapid determination of time-critical parameters (e.g. blood glucose, cardiac markers, blood gases, etc.) can accelerate decision making in the emergency room, intensive care units or even in the primary care setting.

Major benefits are obtained when the output of a POCT device is made available immediately. Results can be shared instantaneously with all members of the medical team enhancing communication by decreasing turnaround time (TAT).

POCT has become established worldwide and finds vital roles in public health. Potential operational benefits of POCT include: faster decision making, reduced operating times, postoperative care time, reduced emergency room time, reduced number of outpatient clinic visits, reduced number of hospital beds required, more optimal use of professional time.

While there are many benefits of using POCT devices in terms of their convenience, establishing POCT is challenging. Some of the biggest challenges relate to engaging health care providers as testing personnel, all the while ensuring adherence to best laboratory practices and regulatory agency standards. Thus POCT implementation requires a systematic approach that involves all stakeholders.

Therefore, there is a need for a POC system and method that provide convenient, assisted workflow solutions for the configuration management of POC analyzers to enable efficient replacement of POC analyzers and to enable traceable relocation of POC analyzers within, for example, a hospital.

SUMMARY

According to the present disclosure, a point of care (POC) testing system and method are presented. The POC system can comprise one or more POC analyzer(s) for analyzing one or more patient sample(s). The one or more POC analyzer(s) can each have an analyzer identifier for identifying the one or more POC analyzer(s). The POC system can also comprise a portable computing device configured to identify the one or more POC analyzer(s) based on the corresponding analyzer identifier. The portable computing device can have a user interface configured to receive a configuration command. The portable computing device can generate a configuration request according to the configuration command. The configuration request can comprise the analyzer identifier(s) of the identified POC analyzer(s). The POC system can also comprise a server for storing system parameter(s) corresponding to the one or more POC analyzer(s). The portable computing device can further be configured to transmit the configuration request to the server. The server can be configured to receive the configuration request, update at least one system parameter corresponding to at least one identified POC analyzer(s), and transmit an analyzer update command comprising at least one analyzer parameter update to at least one identified POC analyzer(s). Finally, the POC system can also comprise a communication network configured to communicatively connect the one or more POC analyzer(s) and the portable computing device with the server. The one or more POC analyzer(s) can be configured to receive the analyzer update command and to update at least one analyzer parameter according to the corresponding analyzer parameter update Accordingly, it is a feature of the embodiments of the present disclosure to provide convenient, assisted workflow solutions for the configuration management of POC analyzers to enable efficient replacement of POC analyzers and to enable traceable relocation of POC analyzers within, for example, a hospital. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
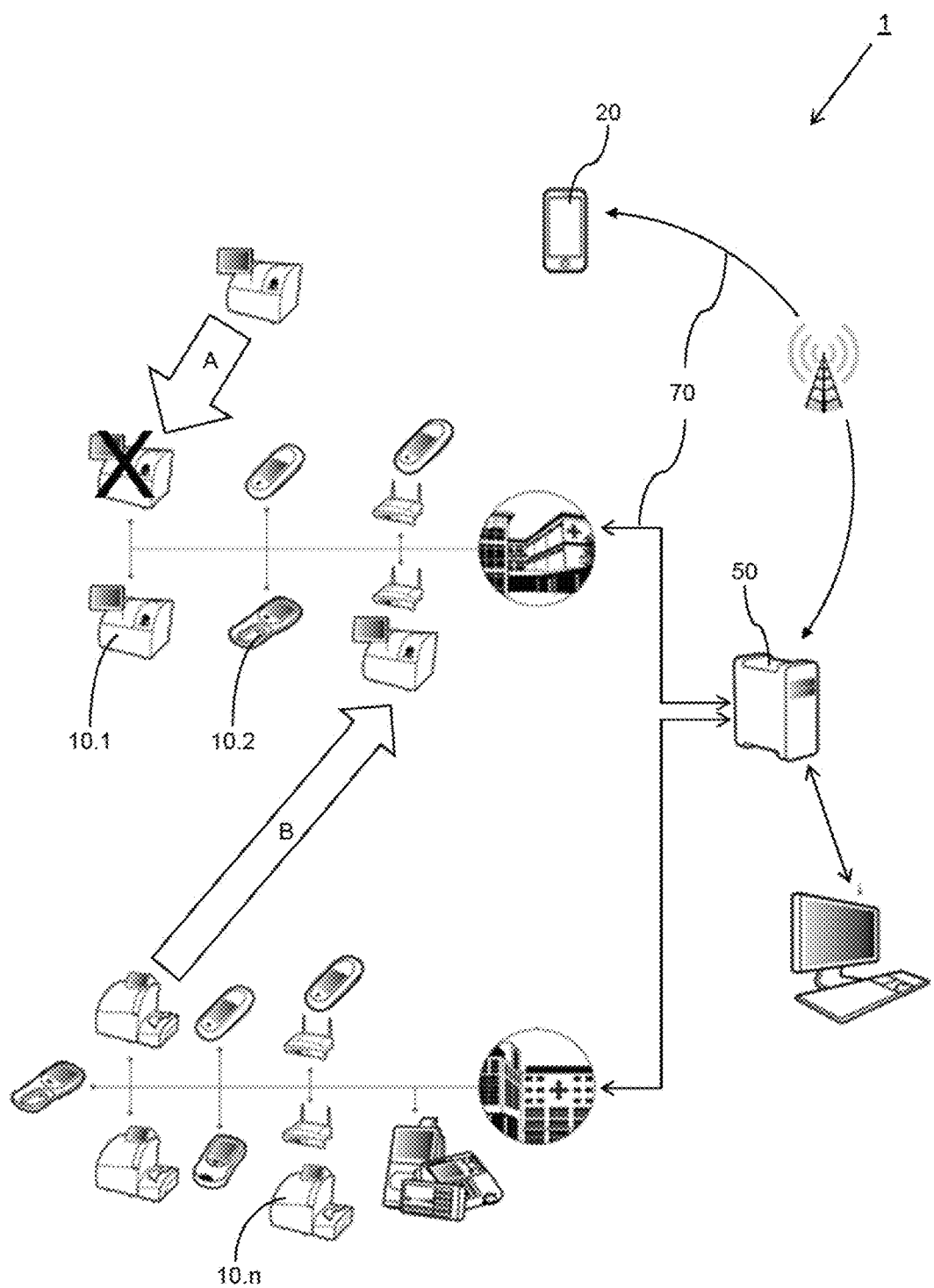
FIG. 1 illustrates a diagram of an embodiment of the point of care POC testing system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Certain terms will be used in this patent application, the formulation of which should not be interpreted to be limited by the specific term chosen, but as to relate to the general concept behind the specific term.

As used herein, the terms 'comprises,' 'comprising,' 'includes,' 'including,' 'has,' 'having' or any other variation thereof, are intended to cover a non-exclusive inclusion.

The terms 'patient sample' and 'biological sample' can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the sample is suspected to contain a certain antigen or nucleic acid.

The term 'analyzer' as used herein can encompass any apparatus for obtaining a measurement value from a patient sample. For example, the analyzer can measure light absorption, fluorescence, electrical potential or other physical or chemical characteristics of the reaction to provide the measurement data. Often such patient samples can be treated before analytical testing is done. Blood sampled from a patient can be e.g. centrifuged to obtain serum or treated with anti-coagulants to obtain plasma.

Analytical testing by an analyzer can have the goal to determine the presence and/or concentration of an analyte in a patient sample. The term 'analyte' can be a general term for substances for which information about presence and/or concentration is intended. Examples of analytes are e.g. glucose, coagulation parameters, endogenic proteins (e.g. proteins released from the heart muscle), metabolites, nucleic acids and so on. The term 'patient health parameter' as used herein can encompass any aspect of a patient's physiology that can be measurable or indicated by an analysis of a patient sample for one or more analyte.

The term 'analytical data' as used herein can encompass any data that can be descriptive of a result of a measurement of one or more patient health parameter(s) performed by a point-of-care (POC) analyzer of the biological sample that has been analyzed. In case of a calibration, the analytical data can comprise the calibration result, i.e. calibration data. In one embodiment, the analytical data can comprise an identifier of the patient sample for which the analysis has been performed and data being descriptive of a result of the analysis, such as measurement data.

The term 'workflow' as used herein can encompass any task carried out by a human or a machine that can comprise one or more steps, such as for maintenance or operation of a system or one of its system components.

The term 'step of a workflow' as used herein can encompass any activity belonging to a workflow.

The term 'authentication data' as used herein can encompass any kind of data suitable to identify an operator/user, such as a user name/user ID and/or password, a security token, a biometric identifier(s) or the like.

The term 'authentication and authorization unit' as used herein can encompass any hardware-, firmware- and/or software-based module operable to execute program logic for receiving and processing authentication data. Furthermore the authentication and authorization unit can comprise any hardware-, firmware- and/or software-based module operable to execute program logic for determining, if the authenticated user/operator possesses the authorization to access a requested feature/data/resource/process/or the like.

The term 'point of care' (POC) or 'point of care environment' as used herein can be defined to mean a location on or near a site of patient care where medical or medically related services such as medical testing and/or treatment can be provided, including but not limited to hospitals, emergency departments, intensive care units, primary care setting, medical centers, patient homes, a physician's office, a pharmacy or a site of an emergency.

The term 'point of care testing' (POCT) as used herein can encompass analysis of one or more patient sample(s) in a point of care environment. POCT can often be accomplished through the use of transportable, portable, and handheld instruments, but small bench analyzers or fixed equipment can also be used when a handheld device is not available—the goal being to collect the patient sample and obtain the analytical data in a (relatively) short period of time at or (relatively) near the location of the patient.

The term 'point of care analyzer' as used herein can encompass any analyzer used in a point of care environment, such as (but not limited to) blood glucose testing, coagulation testing, blood gas and electrolytes analysis, urinalysis, cardiac markers analysis, hemoglobin diagnostics, infectious disease testing, cholesterol screening or nucleic acid testing NAT. Results may be viewed directly on the POC analyzer(s) or may be sent to the POCT system and displayed in a Laboratory Information System (LIS) with central lab results, or alongside imaging results in a Hospital Information System (HIS).

The term 'portable computing device' as used herein can encompass any electronic appliance that can be moved from one location to another appliance without the need of using a tool or to sever a connection of the appliance with another, in particular any handheld battery powered mobile appliance, including but not limited to a cellular telephone, a satellite telephone, a pager, a personal digital assistant ("PDA"), a smartphone, a navigation device, a smartbook or reader, a combination of the aforementioned devices, a tablet computer or a laptop computer.

The term 'communication network' as used herein can encompass any type of wired or wireless network, including but not limited to a WIFI, GSM, UMTS or other wireless digital network or a wired network, such as Ethernet or the like. For example, the communication network may include a combination of wired and wireless networks.

The term 'server' as used herein can encompass any physical machine or virtual machine having a physical or virtual processor, capable of accepting requests from and giving responses accordingly. It can be clear to a person of ordinary skill in the art of computer programming that the term machine may refer to a physical hardware itself, or to a virtual machine such as a JAVA Virtual Machine (JVM), or even to separate virtual machines running different Operating Systems on the same physical machine and sharing that machine's computing resources. Servers can run on any computer including dedicated computers, which individually are also often referred to as 'the server' or shared resources such as virtual servers. In many cases, a computer can provide several services and have several servers running. Therefore the term server can encompass any computerized device that shares a resource to one or more client processes.

The term 'server interface' as used herein can encompass any hardware-, firmware- and/or software-based module operable to execute program logic to allow communication with an external entity (such as a server or another interface).

The term 'user interface' as used herein can encompass any suitable piece of software and/or hardware for interactions between an operator and a machine, including but not limited to a graphical user interface for receiving as input a command from an operator and also to provide feedback and convey information thereto. Also, a system/device may expose several user interfaces to serve different kinds of users/operators.

In the field of bedside testing or point of care testing, the testing can be done on patients typically by nurses, medical staff or doctors but also pharmacists who can be collectively called 'operator(s)' herein. However, anyone who possesses the required certification may be an operator. A point of care coordinator (POCC) may be at the same time an operator of POC analyzer(s) and also an operator of POC analyzer(s) may be at the same time a point of care coordinator (POCC) and thus user of portable computing device(s).

The term 'certification' as used herein can encompass any form of confirmation of certain characteristics (such as training and/or examination and/or educational background and/or accreditation) of an operator. In particular a certification as disclosed herein may not be restricted to embodiments which are formally titled "certification" or physical embodiments (such as a printed certification) having a related title. According to some embodiments, certification(s) can be provided by an entry of an operator on list(s) of certified operators allowed to perform a job/task/ workflow or step of a workflow using one or more of the POC analyzers. The certification(s) according to some embodiments may be permanent and/or time-restricted certifications, meaning that the certification corresponding to an operator can become invalid after a certain period of time. After a certification becomes invalid, the respective operator may need to become certified again (by taking a training and/or passing a (re)examination), otherwise that operator may no longer use the respective POC analyzer(s) or certain features/functions thereof. The term 'system certification' as used herein can encompass a certification stored on a server. According to some embodiments, the system certification can relate to all POC analyzers of the POC testing system. According to further embodiments, the system certification can relate to one or more POC analyzers of a certain type, class, namely POC analyzers having at least one common characteristic. Examples of common characteristics of one or more POC analyzers are: POC analyzers being capable of performing the same or similar analyses of patient sample(s); POC analyzers requiring the same or similar operator training/examination/certification; POC analyzers from one manufacturer; POC analyzers at the same healthcare facility, etc. The term 'analyzer certification' as used herein can encompass any certification stored on a POC analyzer. According to some embodiments, the analyzer certification can store any kind of representation of the operators (such as a list of operator identifiers) authorized to perform at least one job/task/workflow or step of a workflow using that particular POC analyzer, in particular operators authorized to analyze one or more patient sample(s) using that particular POC analyzer. According to certain embodiments, each analyzer certification can be specific to one particular POC analyzer. According to further embodiment(s), each analyzer certification can be specific to one or more POC analyzers of a certain type, class. According to even further embodiment(s), the analyzer certification(s) may be identical to the system certification(s), but stored locally on the POC analyzer(s).

Since POCT performed near the patient can lead directly to diagnostic and therapeutic decisions, a POCT system can advantageously meet multiple requirements (similar to requirements in laboratory testing, but often within shorter times). Examples of such requirements include:

Provide accurate and timely analyses and associate them with the correct patient;

Ensure that operators are competent/certified for the use of the POCT system;

Ensure proper operation, availability and configuration of the analyzers;

Provide reports that are useful to the clinician treating the patient; and

Document testing and Quality Control QC for audit purposes.

POCT can be performed using various POC analyzers such as (but not limited to) analyzers for glucose, coagulation, blood gas, urinalysis, cardiac and molecular testing. Results may be viewed directly on the POC analyzer(s) or may be sent to the POCT system and displayed in a Laboratory Information System (LIS) with central lab results, or alongside imaging results in a Hospital Information System (HIS).

POC analyzers can commonly be managed by a server, and in particular, a hardware management server, also called Point of Care Data Management System (POC-DMS). Such a server can provide connectivity for POC analyzers and management of test results, operators, quality controls, and analyzers.

Management of POCT can be challenging—there can be dozens of sites, hundreds of POCT devices/kits, and thousands of operators to manage to assure quality of testing. One challenge in developing a strategy to manage POCT usually can involve building a competent interdisciplinary POC management team including the laboratory, physicians, and nurses. The POC team can usually hold the responsibility for determining the test menu, selecting technologies, establishing policies and procedures, ensuring training and regulatory compliance, and providing advisory assistance to the end operators of POC technologies. After establishing a POC team, a management structure can often be built that is responsible to implement new initiatives and to perform corrective action where necessary. The POC analyzers of a POCT system can generally be managed by one or more Point of Care Coordinator(s) (POCC). The POCC can be responsible for ensuring that all analyzers are up and running; that all operators are able to use the analyzer(s); know where the analyzers and operators are; and make sure to be compliant to the regulatory expectations.

As illustrated on FIG. 1 for example, the point of care (POC) testing system 1 can comprises one or more POC analyzer(s) 10.1-10.*n*, a portable computing device 20 and a server 50 communicatively connected by a communication network 70. In one embodiment, the communication network 70 can be configured to communicatively connect the one or more POC analyzer(s) 10.1-10.*n* and the portable computing device 20 with the server 50.

The POC analyzer(s) 10.1-10.*n* can be provided and configured for analyzing one or more patient sample(s) in order to measure one or more patient health parameter(s). According to some embodiments, POC analyzer(s) 10.1-10.*n* can include transportable, portable, and handheld instruments and small bench analyzers or fixed equipment as well, such as (but not limited to) blood glucose testing, coagulation testing, blood gas and electrolytes analysis, urinalysis, cardiac markers analysis, hemoglobin diagnostics, infectious disease testing, cholesterol screening or nucleic acid testing (NAT). Several functional and/or operational aspects of the POC analyzer(s) 10.1-10.*n* can be configurable/customizable using one or more analyzer parameter(s).

In order to identify a particular POC analyzer(s) 10.1-10.*n*, each can be provided with an analyzer identifier such as, for example, an identifier tag, such as a barcode and/or an RFID tag but can be a serial number as well.

The server 50 can be provided and configured for storing system parameter(s) corresponding to the one or more POC analyzer(s) 10.1-10.*n*. Some of these system parameters are common for more than one POC analyzers while some system parameters are specific to one single individual POC analyzer 10.1-10.*n*.

The at least one system parameter and/or analyzer parameter can include (but are not limited to) one or more of the following:

Analyzer specific parameters:
Formatting setting(s)
Language setting(s),
Date/Time format setting(s)
Shutdown/Sleep/Hibernate/Logout timeout
Connection configuration (e.g. wlan authentication data)
Analyzer Status: in use, backup, etc.
Security parameters
Authentication mechanism
Login mechanism (only user ID, user ID and Pwd or Barcode scanning)
Patient identification/mapping parameters
Patient identification mechanism
Patient ID mapping
Measurement parameters
Default measurement unit(s)
Workflow definitions) (e.g. force having comments on results or set them optional)
Ranges (such as reference ranges)
Quality Control (QC) parameters
QC Lockout
Lot verification
QC result display
Location specific parameters
Physical location: Healthcare Facility, Building, Floor, Unit, Room
Logical location: Emergency room, intensive care units, primary care setting, medical center, patient home, a physician's office, a pharmacy or a site of an emergency
Location-specific authentication and authorization data.

In certain embodiments of the disclosed system/method, the server 50 can be configured to:

retrieve analytical data from the one or more POC analyzer(s) 10.1-10.*n* such as data representing the measurement of patient health parameter(s);

update program data of the one or more POC analyzer(s) 10.1-10.*n* such as a software update.

The block arrows A and B of FIG. 1 illustrate an analyzer replacement respectively an analyzer relocation workflow as described with reference to the use case diagrams of FIGS. 4 and 6.

As shown on FIG. 1, the communication network 70 can be laid out/configured to communicatively connect the one or more POC analyzer(s) 10.1-10.*n* and the portable computing device 20 with the server 50, FIGS. 2A-D illustrate different embodiments thereof.

Figure 2A:
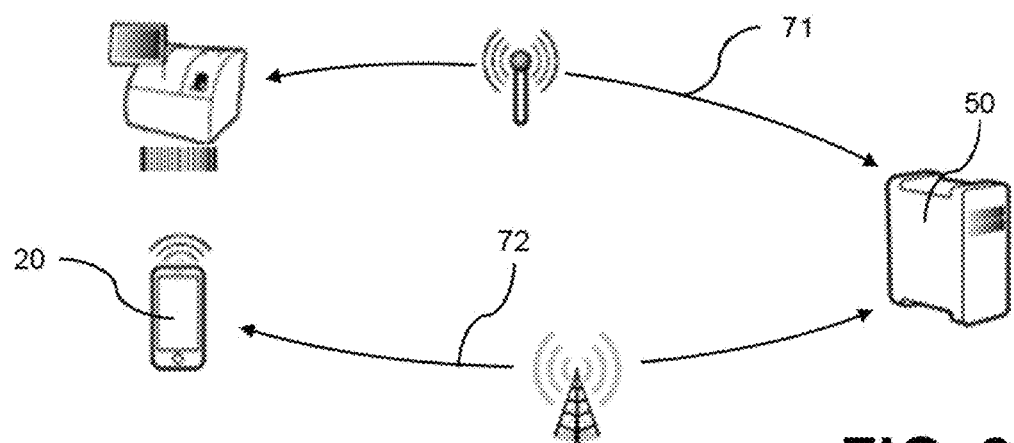
FIG. 2A illustrates an overview of the communication network according to an embodiment of the present disclosure.

FIG. 2A shows a first embodiment of the communication network 70, wherein the portable computing device 20 can be communicatively connected with the server 50 by a remote configuration network area 72, while the one or more POC analyzer(s) 10.1-10.*n* can be communicatively connected with the server 50 using a point of care communication network area 71. According to some embodiments, the remote configuration network area 72 can be a mobile telecommunication network (such as a wireless mobile Internet service, for example, a 3G, 4G or LTE standard) provided by a mobile data carrier service. On the other hand, the point of care communication network area 71 (of some embodiments of the communication network 70) can be a separate network, for example a combination of wired and wireless networks, wherein the healthcare facilities (such as different locations/buildings/floors) can be linked by a wired communication network while the individual POC analyzer(s) 10.1-10.*n* can connect via wireless access points in-between.

As shown on FIG. 2A, according to certain embodiments, there can be no need for a communication between the portable computing device 20 and the POC analyzer(s) 10.1-10.*n* as the (re)configuration thereof is always carried out via the server 50.

Figure 2B:
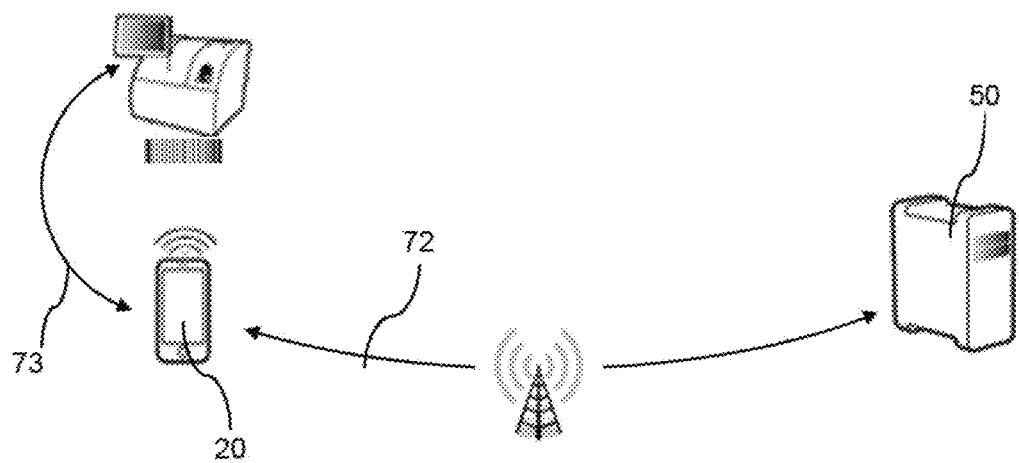
FIG. 2B illustrates an overview of another communication network according to an embodiment of the present disclosure.

Nevertheless, according to another embodiment of the communication network 70, as illustrated on FIG. 2B, the portable computing device 20 and the POC analyzer(s) 10.1-10.*n* can be communicatively connected by a portable device to analyzer network area 73. In this case, the portable computing device 20 can act as a router/access point for the POC analyzer(s) 10.1-10.n, "sharing" its network connection therewith. This embodiment can be advantageous in use scenarios when the POC analyzer(s) 10.1-10.n do not have direct communication with the server 50. This can be the case for example in remote areas where the POC analyzers 10.1-10.n cannot be connected to a point of care communication network area 71 (or not all of them), but the portable computing device 20 does have a network connection via the remote configuration network area 72. In other cases, it might not be economic to provide each POC analyzer with a network connection. In further embodiment, where the portable computing device 20 does have a network connection via the remote configuration network area 72 but not each POC analyzer, can be an emergency response, in which case, the POC analyzers 10.1-10.n may need to be deployed "in the field" in a short period of time. The disclosed system/method can be advantageous in such scenarios as well, since even without each POC analyzer 10.1-10.n having a network connection of their own, they can all be configured easily and consequently from a portable computing device 20, only the portable computing device 20 may need a network connection.

Figure 2C:
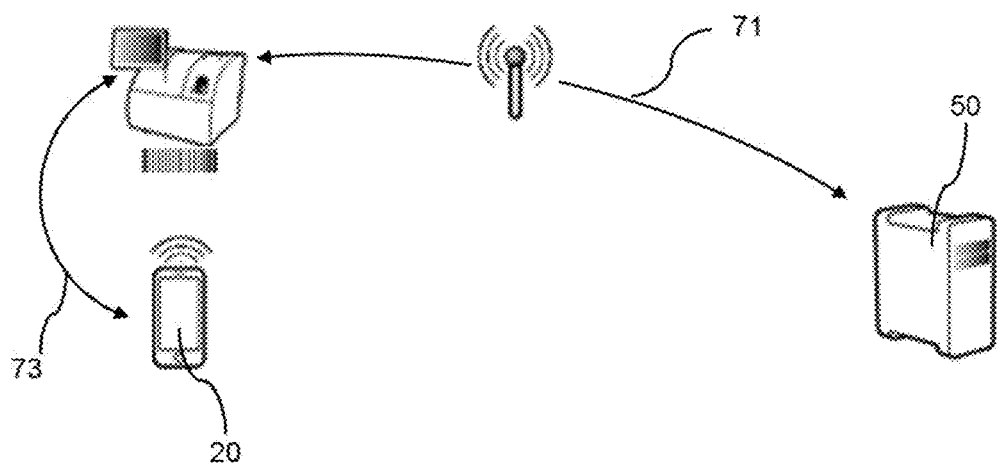
FIG. 2C illustrates an overview of a yet another communication network according to an embodiment of the present disclosure.

FIG. 2C shows a further embodiment of the communication network 70; where a portable device to analyzer network area 73 can be provided to communicatively connect the portable computing device 20 with a POC analyzer 10.1-10.n. In this embodiment, the portable computing device 20 may not be directly connected with the server 50, but via the portable device to analyzer network area 73, the POC analyzer(s) 10.1-10.n acting as a router/access point for the portable computing device 20, "sharing" their network connection therewith. This embodiment can be advantageous in POC environments where the POC analyzers 10.1-10.n are already communicatively connected with the server 50 but there is no mobile telecommunication network (no signal) for the portable computing device 20 to connect to the server 50. For example, there can be POC environments where a mobile telecommunication network may not be desired/permitted, the POC analyzer(s) 10.1-10.n being connected to the server 50 with a wired point of care communication network area 71. Nevertheless, a direct communication between the portable computing device 20 and the POC analyzer(s) 10.1-10.n (for example via Bluetooth or IR) can still be possible/allowable.

Figure 2D:
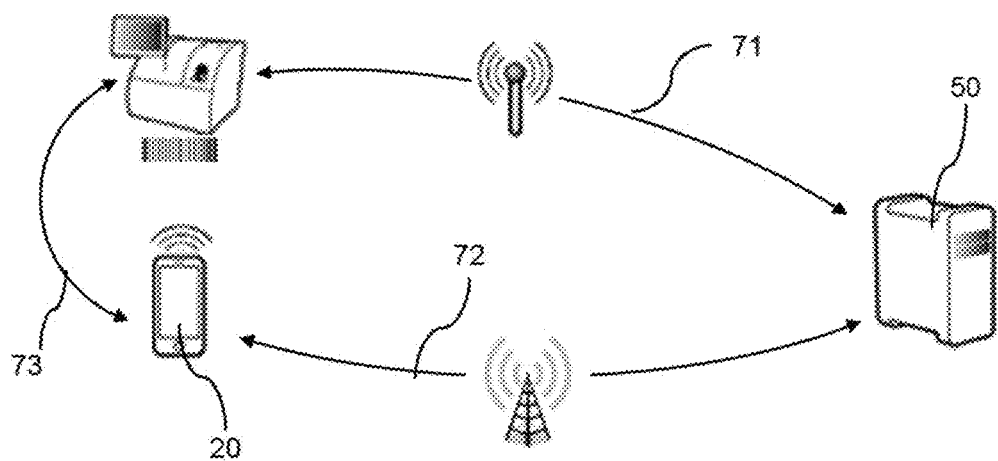
FIG. 2D illustrates an overview of a yet still another communication network according to an embodiment of the present disclosure.

FIG. 2D shows a further embodiment of the communication network 70, where, in addition, to a remote configuration network area 72 and a point of care communication network area 71, a portable device to analyzer network area 73 can also be provided. This embodiment can provide both flexibility and redundancy for the communicative connection of the one or more POC analyzer(s) 10.1-10.n and the portable computing device 20 with the server 50.

It may be pointed out however, that the particular implementation of the communication network 70 (as illustrated on FIGS. 2A-D) is to a certain degree transparent to the POC testing system 1 and may not negatively affect the disclosed configuration method(s) as all embodiments of the communication network 70 disclosed herein can be configured to communicatively connect the one or more POC analyzer(s) 10.1-10.n and the portable computing device 20 with the server 50, be it directly or via different network area(s), such as the point of care communication network area 71 and/or the remote configuration network area 72 and/or the portable device to analyzer network area 73.

Figure 3:
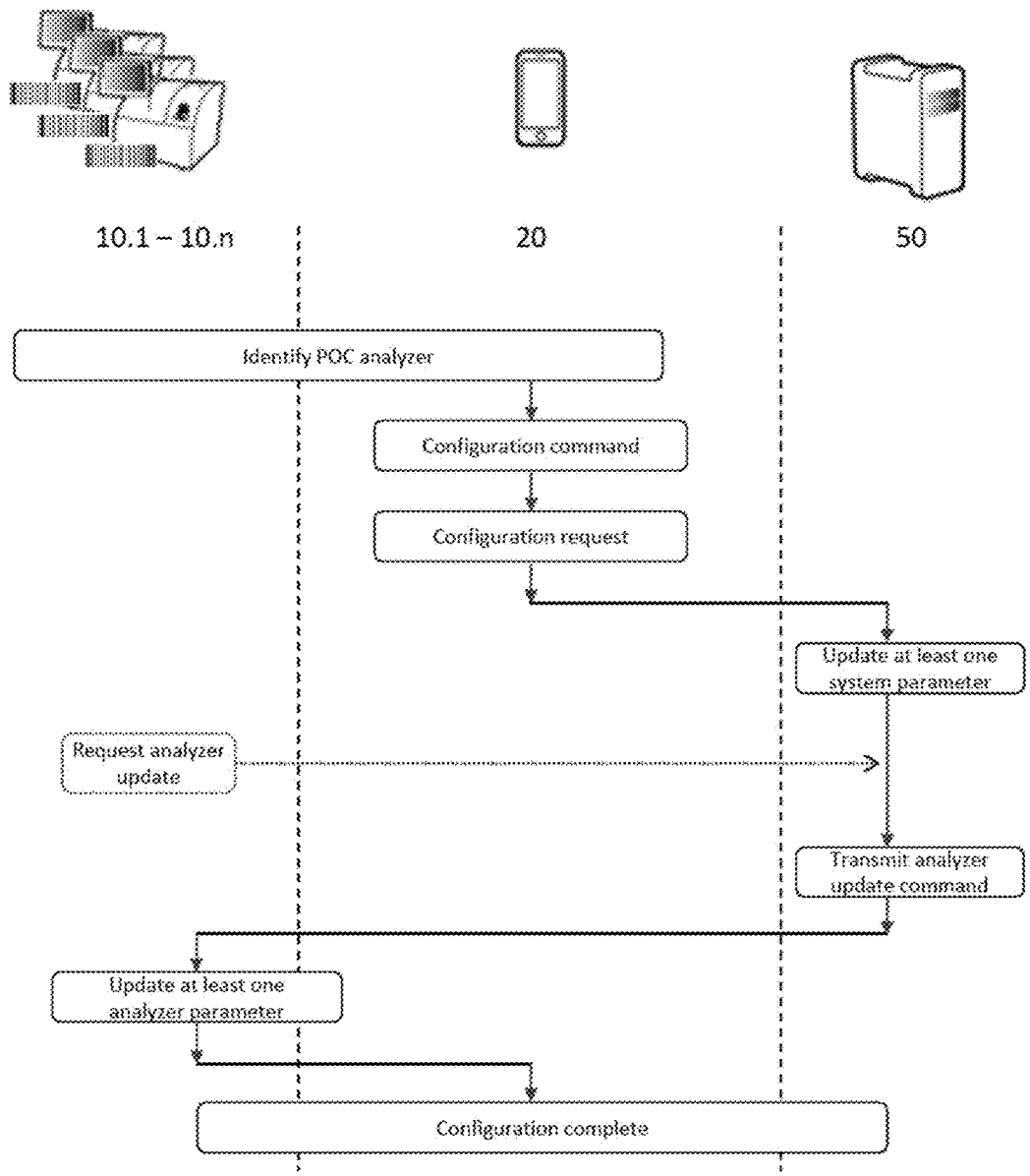
FIG. 3 illustrates a use case diagram of the method for configuration of a point of care POC testing system according to an embodiment of the present disclosure.

FIG. 3 shows a use case diagram of an embodiment of the method for configuration of a POC testing system 1. The symbols on the top of the diagram illustrate the actors of the workflow—the POC analyzers 10.1-10.n, the portable computing device 20 and the server 50, while the steps of the workflow are shown below, illustrating the "involvement" of the actors in the respective workflow step(s). Workflow steps of some embodiment(s) only are illustrated with dotted lines.

In one step, the portable computing device 20 can identify the POC analyzer(s) 10.1-10.n based on the respective analyzer identifier. Corresponding to the particular analyzer identifier, the portable computing device 20 can comprise an identifier reader such as a barcode reader and/or an RFID reader to read the identifier tag and/or a user interface for inputting a serial number of the one or more POC analyzer(s) 10.1-10.n. Alternatively an imaging device (such as a camera) of the portable computing device 20 can be configured to identify the POC analyzer(s) 10.1-10.n. It can be noted that the portable computing device 20 can be configured such that it can identify more than one POC analyzer(s) 10.1-10.n at the same time or successively and thus initiate a reconfiguration of more than one POC analyzers 10.1-10.n at the same time. The more than one POC analyzers 10.1-10.n identified can be referred to as the identified POC analyzer(s) 10.1-10.n.

In order to initiate/start a configuration workflow (process), a configuration command can be given (by an operator). Therefore, the portable computing device 20 can be provided with a user interface 22 configured to receive the configuration command. According to some embodiments of the user interface 22, the configuration command may be a push of a button (physical or screen button) a voice command, a selection in a menu, etc. The configuration command may be any form of input from an operator to initiate a configuration workflow (process).

Triggered by the configuration command, the portable computing device 20 can generate a configuration request comprising the analyzer identifier of the identified POC analyzer(s) 10.1-10.n. After generating it (optionally after confirmation from the operator), the portable computing device 20 can transmit the configuration request to the server 50. Therefore, the configuration request can be described as a sort of translation of the configuration command from the operator into a request signal to the server 50.

The server 50 can be configured to receive the configuration request, the transmission thereof being performed using the communication network 70. After receiving it, the server 50 can:

update at least one system parameter corresponding to the identified POC analyzer(s) 10.1-10.n; and transmit an analyzer update command comprising at least one analyzer parameter update to the identified POC analyzer(s) 10.1-10.n.

The above steps by the server 50 will now be described in greater detail. On one hand, the server 50 can be configured to update at least one system parameter corresponding to the identified POC analyzer(s) 10.1-10.n. The server 50 can retrieve (can look up) the corresponding system parameter(s) as the configuration request generated by the portable computing device 20 can comprise the analyzer identifier(s). Depending on the configuration command/ configuration request, the server 50 can update the appropriate system parameter(s).

In order to ensure that the configuration command (as a complete workflow) is implemented not only on the server 50 but across the POC testing system 1, the server 50 can be configured to transmit an analyzer update command(s) comprising at least one analyzer parameter update to the identified POC analyzer(s) 10.1-10.$n$ which, in turn, can be configured to receive the analyzer update command and to update at least one analyzer parameter according to the corresponding analyzer parameter update. According to some embodiments and according to the particular POC analyzer(s) 10.1-10.$n$, the updating of an analyzer parameter may become effective immediately, upon the next start-up/restart/docking etc. of the analyzer.

In other words, the configuration command given via the user interface 22 of the portable computing device 20 can initiate a system-wide configuration workflow, wherein within the configuration workflow, the portable computing device 20, the server 50 and the POC analyzers 10.1-10.$n$ can collaborate (via the communication network) to ensure that required parameters (system parameters and analyzer parameters alike) can be updated across the POC testing system 1. This approach can have the advantage that a single configuration command can be given from a remote location (remote meaning a location different from the server) in order to (re)configure the POC testing system 1—including any number of POC analyzers, the POC testing system 1 being configured such as to implement the configuration command without the need for additional actions/steps by the operator. Thus both operator effort and probability of operator error can be greatly reduced, as there is no need for the operator to individually update system parameters on the server 50, identify the corresponding analyzer parameters and then update the respective POC analyzers 10.1-10.$n$. These steps can be taken over by the system/method. Therefore, some embodiments can be particularly advantageous over existing solutions, which commonly perform only the update of the system parameters on a server, wherein the operator is responsible to perform the update of the analyzer parameters of the respective POC analyzer(s).

According to some embodiments, the steps of:
the server 50 transmitting an analyzer update command;
the POC analyzer(s) 10.1-10.$n$ receiving the analyzer update command; and
the POC analyzer(s) 10.1-10.$n$ updating of at least one analyzer parameter can be initiated by one or more POC analyzer(s) 10.1-10.$n$ requesting an analyzer update. Correspondingly, the one or more POC analyzer(s) 10.1-10.$n$ can be configured to request an analyzer update on occurrence(s) of certain event(s) and/or at regular intervals. According to some embodiments, such event(s) can comprise (but are not limited to) a login by an operator; a startup/shutdown/docking/undocking (into a docking station) of the POC analyzer 10.1-10.$n$. According to some embodiments, the regular intervals (when the one or more POC analyzer(s) 10.1-10.$n$ are configured to request an analyzer update) can be chosen to coincide with work shift changes of the operators or with time intervals when—based on historical data—the POC analyzers are least expected to be used. Thus the regular intervals can be configured such as to minimize unavailability (or predicted unavailability) of the POC analyzer(s) 10.1-10.$n$.

To summarize the analyzer update(s)—according to some embodiments—the analyzer update(s) may be implemented using "server push" technology (that is server initiated) and/or a "client pull" technology (client—in this case POC analyzer initiated). The server push implementation of the analyzer update can be advantageous for POC analyzers 10.1-10.$n$ which are continuously communicating with the server 50, while the client pull implementation of the analyzer update can be advantageous for POC analyzers 10.1-10.$n$ which communicate with the server 50 only on an event basis, such as periodically and/or upon a login by an operator and/or upon startup and/or upon shutdown of the respective POC analyzer 10.1-10.$n$.

Some embodiments can be particularly advantageous as they can allow a decentralized control of POC analyzers by a portable computing device. The disclosed solution can allow communication with hardware management software (such as the COBAS IT 1000 of Roche Diagnostics) through a portable computing device, making it possible to (re)configure POC analyzer(s) and at the same time can also initiate the corresponding server update(s). This combined update of both system parameter(s) and analyzer parameter(s) can ensure consistent (re)configuration of the POC testing system within a single workflow.

A common task of a POCC can be the relocation of a POC analyzer(s), necessary due to changed organizational structure or workload fluctuations within the healthcare facilities. The physical relocation of a POC analyzer(s) usually can also trigger the need to update corresponding settings of the server (hardware management server) and also reconfiguration of one or more parameters of the POC analyzer(s). For example, when a POC analyzer(s) is relocated from a children's hospital ward to an adult's ward, certain parameters of the POC analyzer(s) may need to be updated accordingly to ensure the analyzer provides accurate results. Furthermore, not only parameters of the POC analyzer(s) but also settings of the server (hardware management server) may need to be updated to reflect the change in authorization of the use of the respective POC analyzer(s) by personnel in the adult's ward authorized to perform diagnostic procedures on adult's samples.

Using known POC testing systems managed by known servers (hardware management server), the POCC may need to catalog all analyzer(s) to be relocated, change their corresponding settings in the server (hardware management server) at his workstation. Also, the POCC may need to physically locate each POC analyzer(s), change their respective settings to reflect the relocation. This process may be not only time-consuming but also error prone. Therefore, the POCC has no convenient and efficient means to replace a non-functional POC analyzer(s) with a backup analyzer(s) using known point of care (POC) testing systems. While this process is feasible in a healthcare facility with a limited number of analyzers, it can be a real challenge when a POCC is responsible for hundreds if not thousands of POC analyzers.

However, none of the known systems offer convenient workflow(s) to (re)configure POC analyzers remotely, (re)configuration workflow(s) such as relocation of one or more POC analyzer(s) or replacement of non-functional POC analyzer(s) with backup analyzer(s).

According to further embodiments, the configuration command can comprise a relocation command corresponding to a relocation of one or more POC analyzer(s) 10.1-10.$n$, which can be transmitted to the server 50, which can update one or more system parameter(s) in accordance with the relocation of the identified POC analyzer(s) 10.$n$-10.$n$ and can retrieve at least one analyzer parameter update in accordance with the relocation of the identified POC analyzer(s) 10.$n$-10.$n$ to be transmitted within the analyzer parameter update to the identified POC analyzer(s) 10.$n$-10.$n$.

Figure 4:
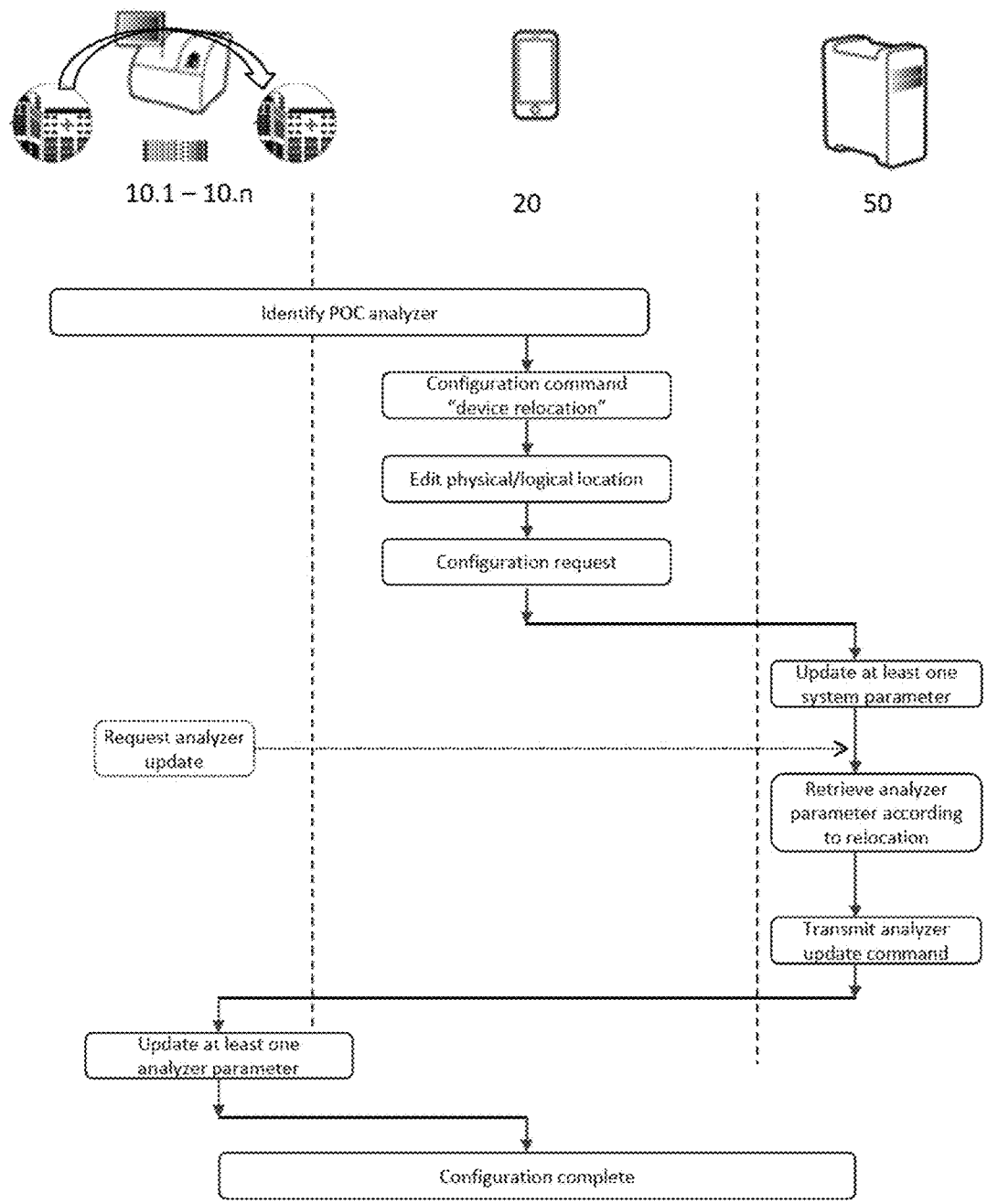
FIG. 4 illustrates a use case diagram of the method for configuration of a point of care POC testing system, illustrating relocation of a POC analyzer according to an embodiment of the present disclosure.

FIG. 4 shows a use case diagram of an embodiment for configuration of a POC testing system 1, illustrating a relocation workflow of a POC analyzer 10.1-10.$n$. The relocation can comprise both a physical and/or logical relocation of one or more POC analyzer(s) 10.1-10.$n$. For example, a physical relocation can refer to a change of physical location from one healthcare facility/building/building floor etc. to another. On the other hand, the logical relocation can refer to a change in the reassignment of one or more POC analyzer(s) 10.1-10.*n*, for example, between different hospital wards, emergency departments, intensive care units, primary care setting, medical centers, patient homes, a physician's office, a pharmacy or a site of an emergency.

Figure 5A:
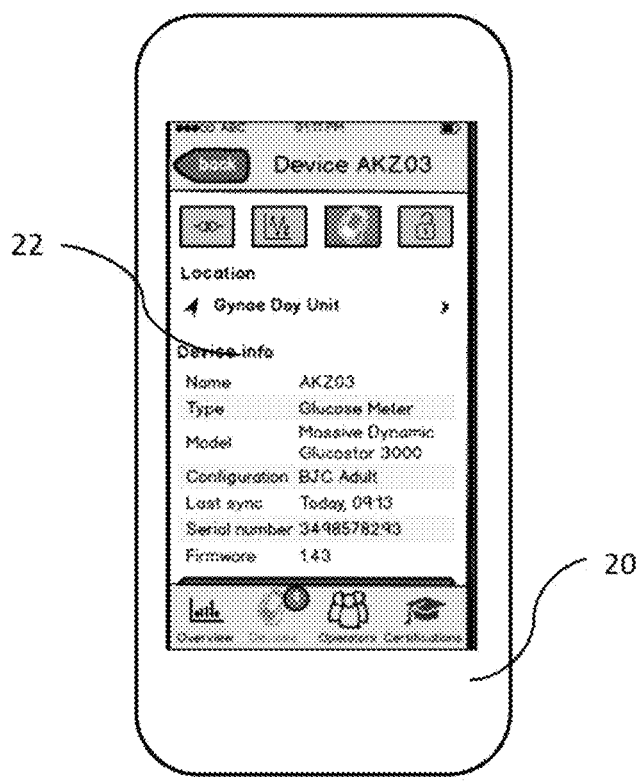
FIGS. 5A-B illustrate screenshots of a portable computing device; illustrating method steps of a relocation of a POC analyzer according to an embodiment of the present disclosure.
Figure 5B:
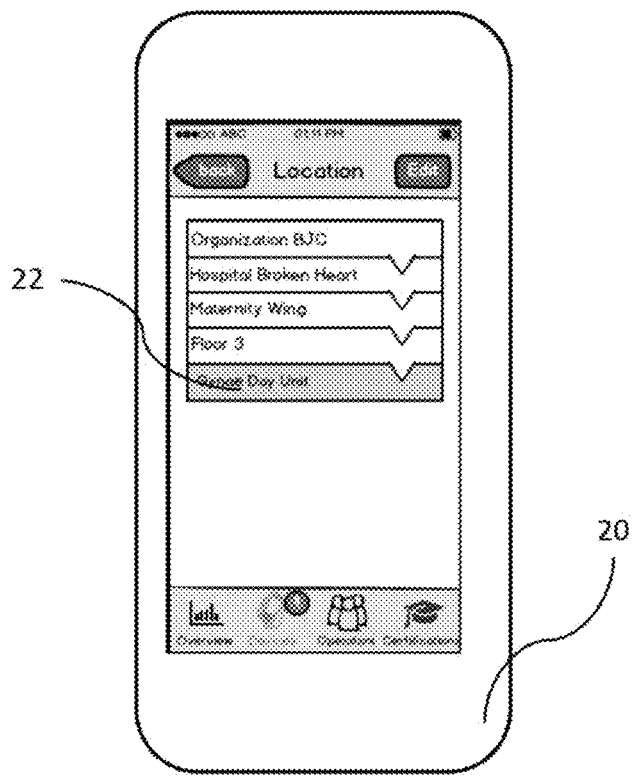

As shown on the use case diagram of FIG. 4 and the screenshots of FIGS. 5A-B, the configuration command received by the portable computing device 20 can comprise a relocation command corresponding to a relocation of one or more POC analyzer(s) 10.1-10.*n*. This may be in the form of a selection of a physical and/or logical location from a list, a map or manual input of a location or a combination thereof.

As shown on FIG. 4, according to embodiments directed towards a relocation of POC analyzer(s) 10.1-10.*n*, the server 50 can be configured to update one or more system parameter(s) in accordance with the relocation of the identified POC analyzer(s) 10.1-10.*n* and to retrieve at least one analyzer parameter in accordance with the relocation of the identified POC analyzer(s) 10.1-10.*n* to be transmitted within the analyzer parameter update to the identified POC analyzer(s) 10.1-10.*n*. For example, upon receiving a relocation command comprising as new location a children's hospital ward, the server 50 can retrieve all analyzer parameters such as different reference values (as different values apply when analyzing patient samples of children as compared to adults), new workflow definitions (as different locations may use different workflows), new QC parameters, etc. The analyzer parameters retrieved in this step can be referred to as retrieved analyzer parameters.

As a following step, the server 50 can transmit the retrieved analyzer parameter(s) to the POC analyzer(s) 10.1-10.*n* to be relocated (that is the identified POC analyzer(s) 10.1-10.*n* by the portable computing device 20).

One further aspect of the maintenance operations of a POCC can be to replace a non-functional POC analyzer(s) with a backup analyzer(s) and/or to relocate a POC analyzer(s) as needed, these operations including (re) configuration of the respective POC analyzer(s) and the server (hardware management server) according to the replacement/relocation of analyzer(s).

Using available POC testing system(s) managed by known hardware management servers, the POCC can fetch the non-functional POC analyzer(s) and the backup analyzer(s) and change their allocation on the server at his workstation, updating all the corresponding settings so that the backup analyzer(s) take the place of the non-functional POC analyzer(s). Thereafter, the POCC (or an assistant/nurse etc.) may need to take the (now replaced) POC analyzer(s) to the location where it is needed. When a POCC is responsible for hundreds of analyzers possibly at different locations, this can be a tedious and time-consuming task, which can be especially problematic in an environment where clinical decision making in the emergency department, intensive care units or primary care setting is dependent on analysis to be performed by the replacement analyzer.

Alternatively, the operator (an assistant/nurse) of the non-functional POC analyzer(s) can call (or email or notify by other suitable means) the POCC and provide him with the details of the non-functional POC analyzer(s)—such as its identifier (e.g. barcode) so that the POCC can update all the corresponding settings so that the backup analyzer(s) take the place of the non-functional POC analyzer(s). However, this solution can also be time-consuming and error-prone, especially as often it is only the POCC—who already travelled onsite—the one to determine that the POC analyzer(s) is non-functional and needs to be replaced.

Therefore, the POCC can have no convenient and efficient means to replace a non-functional POC analyzer(s) with a backup analyzer(s) using known systems.

According to further embodiments, the configuration command can comprise a replacement command corresponding to a replacement of a first POC analyzer 10.1 (e.g. a broken analyzer) with a second POC analyzer 10.2 (e.g. a replacement analyzer). The replacement command can be transmitted by the portable computing device 20 to the server 50, which can retrieve one or more system parameter(s) corresponding to the first POC analyzer 10.1, can update therewith respective system parameter(s) corresponding to the second POC analyzer 10.2, and can retrieve one or more analyzer parameter(s) corresponding to the first POC analyzer 10.1 to be transmitted within the analyzer parameter update to the second POC analyzer 10.2.

Figure 6:
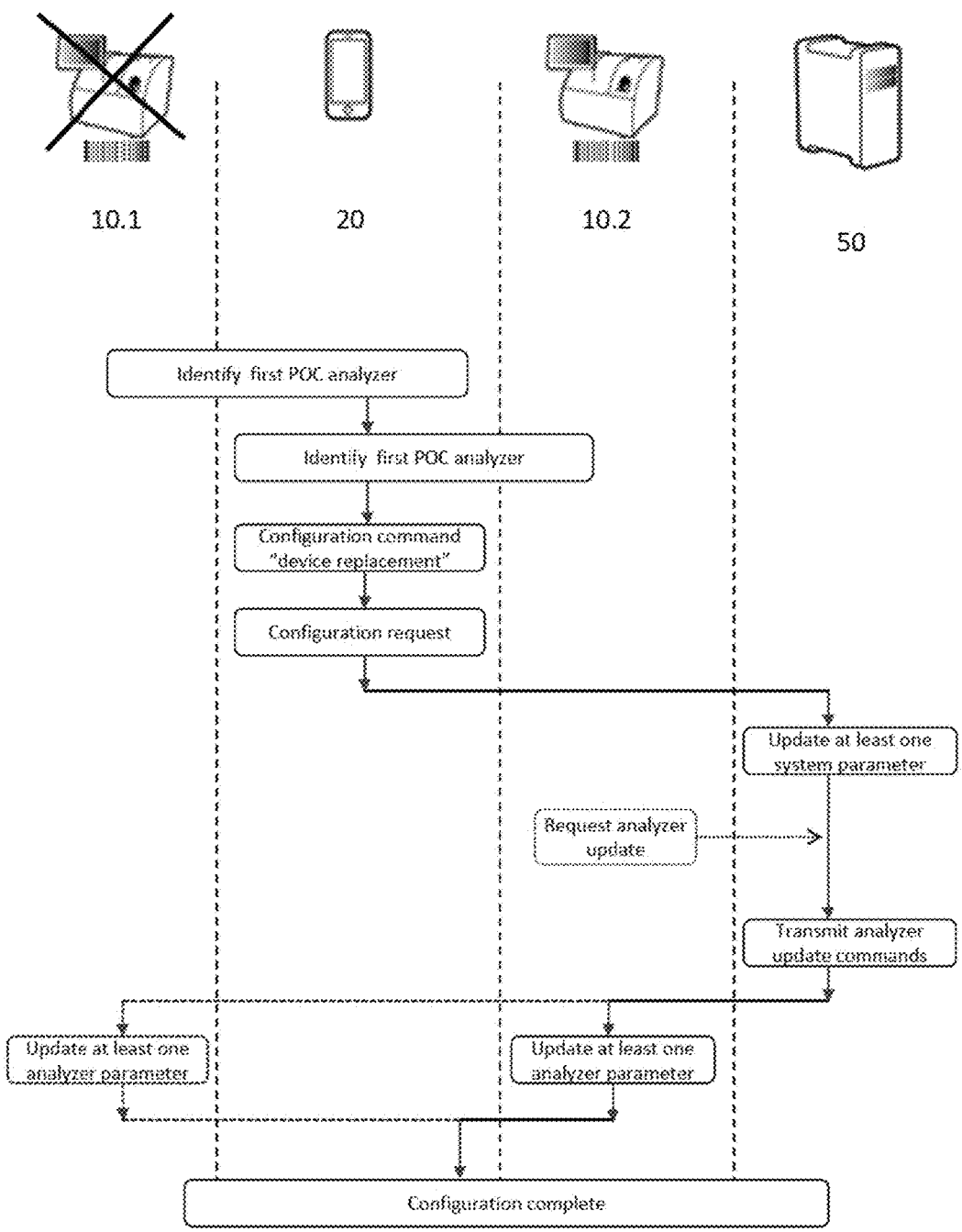
FIG. 6 illustrates a use case diagram of the method for configuration of a point of care POC testing system, illustrating a replacement of a first (defective) POC analyzer with a second (replacement) POC analyzer according to an embodiment of the present disclosure.

FIG. 6 shows a use case diagram of an embodiment illustrating a replacement workflow of a first POC analyzer 10.1 with a second POC analyzer 10.2. The replacement of the first POC analyzer 10.1 may be required for several reasons, including (but not limited to) replacement of a non-functional (broken) or not-fully-functional (partially broken) analyzer with a backup analyzer with identical or at least similar capability(s) of analyzing one or more patient sample(s). The term 'non-functional' or 'not-fully-functional' with reference to a POC analyzer can mean that the particular POC analyzer is at least at that moment not capable to perform or not capable to perform at a required quality/speed at least one of its functions, such as the analysis of a patient sample. Thus the term 'non-functional' or 'not-fully-functional' do not necessarily mean that the POC analyzer is completely defective/broken. Furthermore, the term 'non-functional' or 'not-fully-functional' can comprise software- and/or hardware aspects of non-functionality.

Alternatively, an analyzer may be replaced with a different analyzer which is at the time not in use or when the priority of analyzing more patient sample(s) so requires. In a different usage scenario, the replacement workflow of a first POC analyzer 10.1 with a second POC analyzer 10.2 can be performed within an update/exchange or maintenance of the POC testing system 1.

Figure 7A:
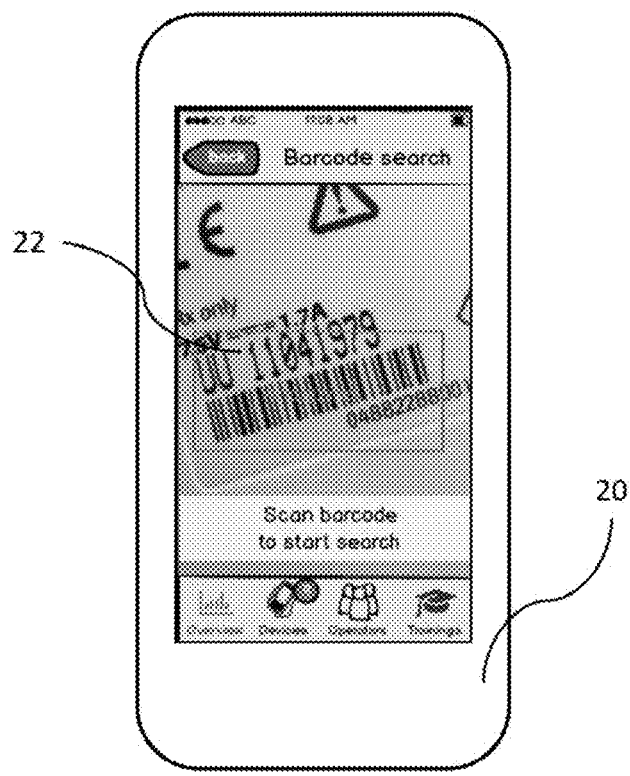
FIGS. 7A-D illustrate screenshots of a portable computing device; illustrating method steps of a replacement of a first (defective) POC analyzer with a second (replacement) POC analyzer according to an embodiment of the present disclosure.
Figure 7B:
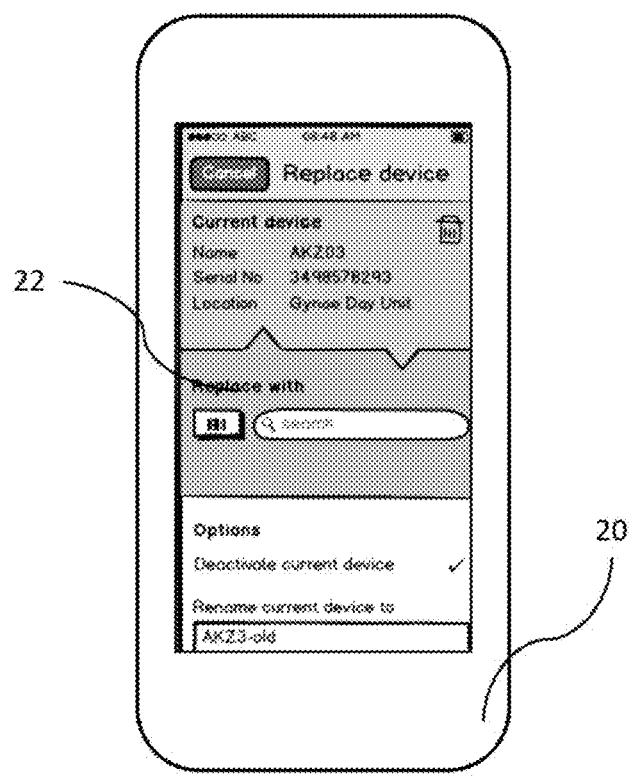
Figure 7C:
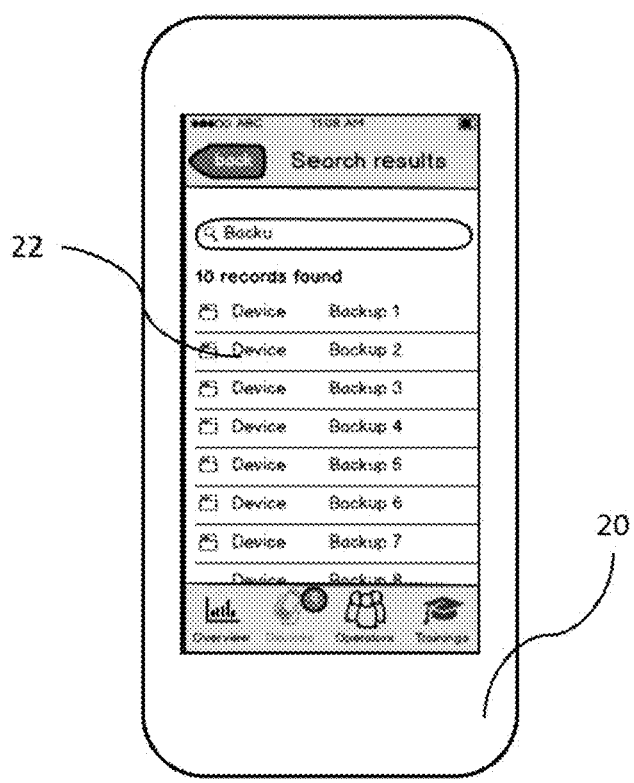
Figure 7D:
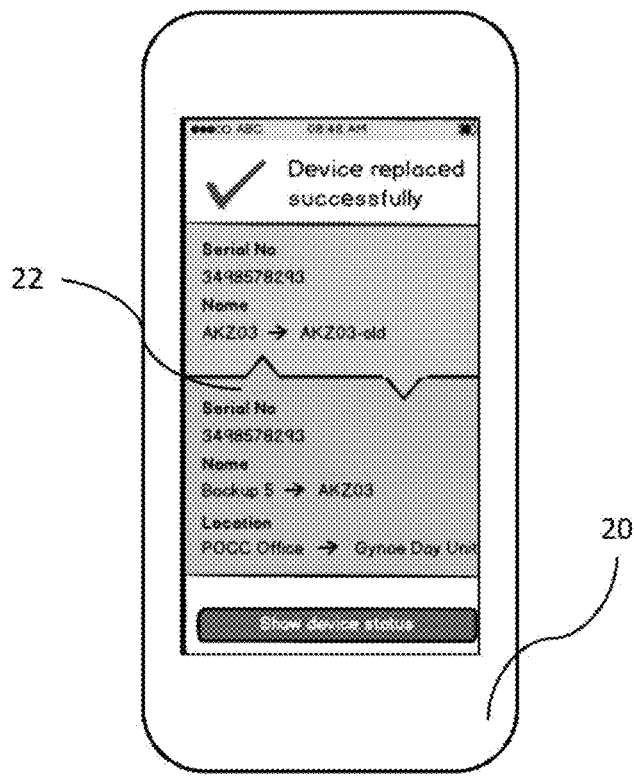

As illustrated in FIG. 6, the portable computing device 20 can identify a first POC analyzer 10.1 which may need to be replaced and a second POC analyzer 10.2 based on the corresponding analyzer identifier(s). Thereafter, the device replacement command can be received (as shown in FIG. 7B) corresponding to a replacement of the first POC analyzer 10.1 with the second POC analyzer 10.2. According to some embodiments, the replacement command can be comprised within the configuration command. Alternatively, a separate command may be given by the operator via the user interface 22.

According to some embodiments, the replacement command can be received before the second POC analyzer 10.2 is identified.

After receiving the replacement command and identifying both the first POC analyzer 10.1 which needs to be replaced and the second POC analyzer 10.2, the portable computing device 20 can generate the configuration request comprising the replacement command and the analyzer identifiers corresponding to the first POC analyzer 10.1 and to the second POC analyzer 10.2.

As shown on FIG. 6, the server 50 can be configured to retrieve one or more system parameter(s) corresponding to the first POC analyzer 10.1 and update therewith respective system parameter(s) corresponding to the second POC analyzer 10.2. The system parameters retrieved in this step can be referred to as retrieved system parameters. In other words, the system parameters corresponding to the first POC analyzer 10.1 can be copied/moved to update the system parameter(s) for the second POC analyzer 10.2. After updating the system parameters, the second POC analyzer 10.2 can take the place of the first POC analyzer 10.1 in the POC testing system 1. However, in order for the replacement to be fully completed and for the operator to perceive and be able to use the second POC analyzer 10.2 as it would be the first POC analyzer 10.1 (at least functionally—in case the two analyzers are not identical in appearance), analyzer parameter(s) corresponding to the first POC analyzer 10.1 can be retrieved by the server 50 and sent to the second POC analyzer 10.2 as analyzer parameter update(s). The analyzer parameters retrieved in this step can be referred to as retrieved analyzer parameters.

Since the second POC analyzer 10.2 can be configured to receive analyzer update command(s) and to update at least one analyzer parameter according to the corresponding analyzer parameter update, the analyzer parameters of the first POC analyzer 10.1 can be copied/moved to the second POC analyzer 10.2.

Therefore, some embodiments directed towards an analyzer replacement can be particularly advantageous as they can provide a simple and efficient workflow solution to replacing a POC analyzer by a single command given on a portable computing device, wherein the system/method can take care of the necessary steps (on the server and the involved POC analyzers) so that thereafter an operator can use the replacement POC analyzer providing the same functionalities and/or same setup/configuration and/or user rights, etc. as the POC device which had to be replaced. This can ensure a very positive user experience as service/maintenance and/or analyzer update activities can be made transparent to the operator and downtime of a particular type of POC analyzer can be eliminated or at least minimized.

According to some embodiments, the server 50 can be configured to flag the first POC analyzer 10.1 as inactive after updating the system parameter(s) corresponding to the second POC analyzer 10.2. The POCC can then inspect POC analyzers flagged or have them inspected by a technician. After repair (hardware and/or software), the inactive flag of the respective POC analyzers can be removed and can become available for use again, be it immediately or as a backup analyzer for use as replacement.

A further challenge in the management of POCT can be posed by the configuration management of operator training and of the corresponding training certification(s). Traditionally, the management of operator training/certification(s) implies that training/certification data has to be entered centrally often even manually in a paper based approach. An obvious consequence of this type of training/certification management is that the probability of an error or delays can be higher. This situation can have a high impact on efficiency and can even create some issues regarding the speed of patient care.

However, the certification management of prior art solutions is performed centrally. This approach has several disadvantages, especially in dynamic point of care environments with a high number of operators requiring training (in the thousands to tens of thousands across multiple healthcare facilities), a high turnover rate of operators who may be transferred between different departments and operators with diverse educational backgrounds. Thus, in comparison with a more static environment where trainings and examinations can be planned in advance and corresponding certificates can be managed centrally, in a dynamic environment there can be a need to be able to perform the management of operator training/certification/status in an ad-hoc manner and if needed both on-site—namely at or near the particular POC analyzer, the patient and/or the healthcare staff (the operator)—or off-site—which may be necessary in cases when it may not be feasible for the point of care coordinator to relocate (for time/distance/resource constraints).

According to further embodiments, the configuration of the POC testing system 1, in order to manage operator certifications, can be performed as follows:

one or more system certification(s) 30.1-30.m, each corresponding to one or more POC analyzer(s) 10.1-10.n can be stored on the server 50;

operators of the POC testing system 1 can be provided with corresponding operator identifier(s);

one or more certification(s) 30.1-30.m can be selected via the user interface 22 of the portable computing device 20;

one or more operator(s) can be identified using the operator identifier(s);

a certification configuration command can be given via the user interface 22 of the portable computing device 20;

a certification configuration request can be generated by the portable computing device 20, the certification configuration request comprising:

the one or more operator identifier(s) corresponding to the identified operator(s); and data identifying the selected system certification(s) 30.1-30.m;

the server can receive the configuration request;

the server 50 can update the selected system certification(s) 30.1-30.m according to the certification configuration request;

the server 50 can transmit an analyzer certification update for each of the selected system certification(s) 30.1-30.m to the corresponding POC analyzer(s) 10.1-10.n;

the one or more POC analyzer(s) 10.1-10.n can receive the analyzer certification update;

the one or more POC analyzer(s) 10.1-10.n can update their respective analyzer certification according to the analyzer certification update.

Such embodiments can be particularly advantageous for allowing a decentralized control of analyzer certifications and permitting a point of care coordinator to easily add/delete/update operators (their status) to the system. Status update(s) can be related to the completion of training/successful examination or an operator access update. This way such management steps can be done immediately via a portable computing device in an efficient and secure manner.

Figure 8:
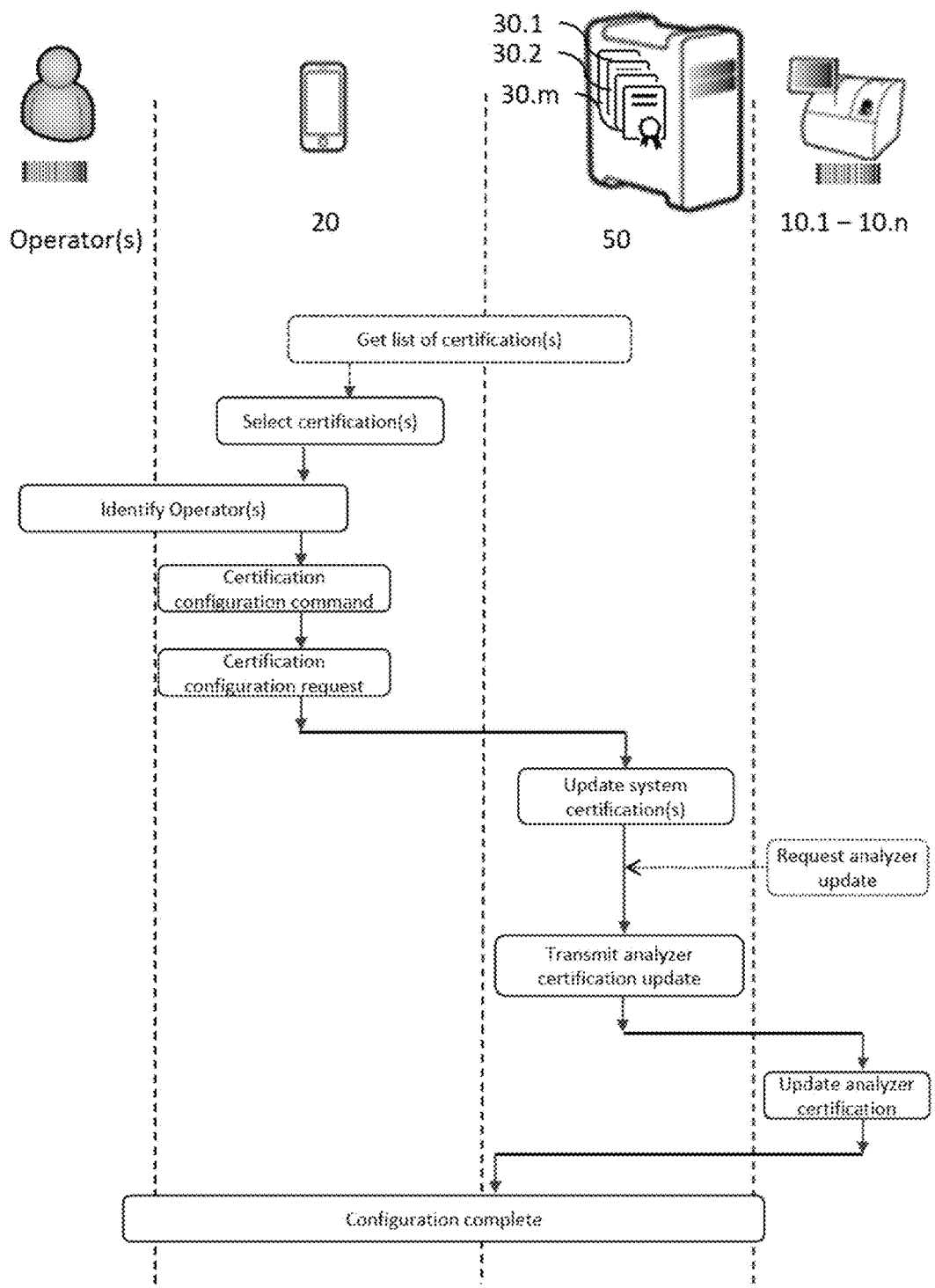
FIG. 8 illustrates a use case diagram of the method for configuration of a point of care POC testing system, illustrating a certification configuration corresponding to one or more operator(s) and one or more certification(s) according to an embodiment of the present disclosure.

FIG. 8 shows a use case diagram of further embodiments of a POC testing system illustrating a certification configuration corresponding to one or more operator(s) and one or more certification(s).

According to some embodiments, the server 50 can further be configured for storing one or more system certification(s) 30.1-30.m, each corresponding to one or more POC analyzer(s) 10.1-10.n. As shown on FIG. 9A, according to some embodiments, the server 50 can be configured to store a system certification 30.1-30.m for each type/class of POC analyzers. For this, analyzers of the same type/class (with similar functionality of analyzing patient sample(s)) can be grouped and a system certification 30.1-30.m can be stored for each type/class, each system certification 30.1-30.m storing the operator identifier(s) of each operator certified to operate one or more POC analyzer(s) 10.1-10.n of the type/class. Alternatively, the server 50 can be configured to store a system certification 30.1-30.m for each of the one or more POC analyzer(s) 10.1-10.n.

In one step (in certain embodiments, the step being shown with dotted lines), the portable computing device 20 can be configured to request the one or more system certifications 30.1-30.m and/or a list of the one or more system certifications 30.1-30.m from the server 50, while the server 50 can be configured to transmit the one or more system certifications 30.1-30.m and/or a list of the one or more system certifications 30.1-30.m to the portable computing device 20.

Figure 9A:
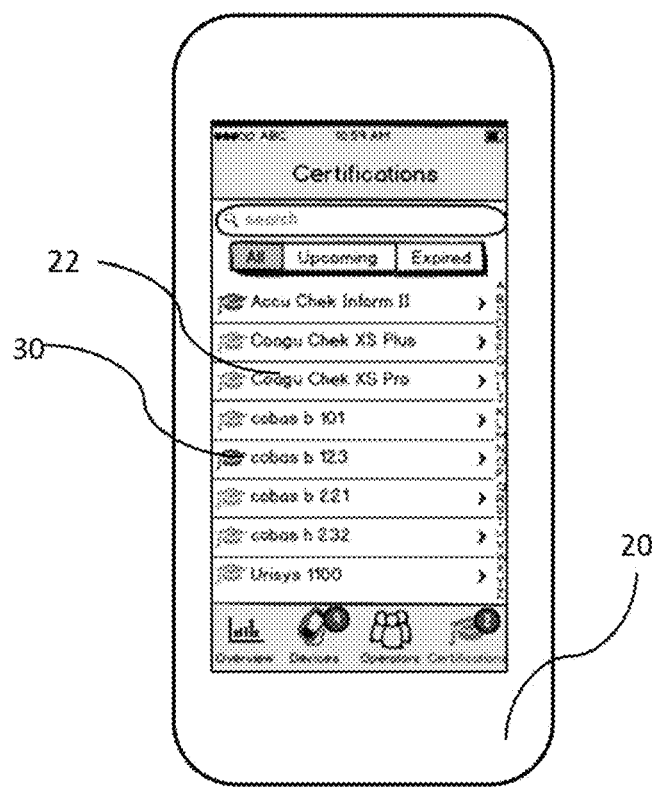
FIGS. 9A-D illustrate screenshots of a portable computing device, illustrating method steps of a certification configuration corresponding to one or more operator(s) and one or more certification(s) according to an embodiment of the present disclosure.

Thereafter, one or more of the system certifications 30.1-30.m can be selected via the user interface 22 of the portable computing device 20 as shown in FIG. 9A, these can be referred to as the selected system certifications 30.1-30.m.

For identifying operator(s) of the one or more POC analyzer(s) 10.1-10.n of the POC testing system 1, operator(s) can be provided with operator identifier(s), each operator identifier uniquely identifying the respective operators. Correspondingly, the portable computing device 20 can be configured to identify one or more operator(s) of the POC testing system 1 using one or more operator identifier(s). The one or more operator(s) identified by the portable computing device 20 can be referred to as the identified operator(s).

According to some embodiments, the one or more operator identifier(s) can be identifier tags, such as a barcode and/or an RFID tag and/or an alphanumeric identifier. Correspondingly, the portable computing device 20 can comprise an identifier reader such as a barcode reader and/or an RFID reader to read the identifier tag and/or input method (such as a keyboard or input field on a screen) for inputting an alphanumeric identifier of the one or more operator identifier(s). In addition or alternatively, a camera device may be provided to identify the operators based on the operator identifier(s). In addition or alternatively, biometric identification of the operator(s) may be used.

After one or more operator(s) have been identified and one or more certifications 30.1-30.m have been selected, a certification configuration command can be received via the user interface 22 of the portable computing device 20. According to embodiments of the user interface 22, the certification configuration command may be a push of a button (physical or screen button) a voice command, a selection in a menu, etc. The certification configuration command may be any form of input from an operator to initiate a configuration workflow (process).

Initiated by the certification configuration command, the portable computing device 20 can generate a certification configuration request comprising:

the one or more operator identifier(s) corresponding to the identified operator(s); and data identifying the selected system certification(s) 30.1-30.m.

According to some embodiments, the certification configuration request transmitted by the portable computing device 20 to the server 50 can comprise one or more of the following:

addition of an operator status corresponding to the identified operator(s); and/or removal of an operator status corresponding to the identified operator(s); and/or update of an operator status corresponding to the identified operator(s).

After generating it (optionally after confirmation from the operator), the portable computing device 20 can transmit the certification configuration request to the server 50. Therefore, the certification configuration request can be described as a translation of the certification configuration command from the operator into a request signal to the server 50.

After receiving the certification configuration request—via the communication network 70—the server 50 can:

update the selected system certification(s) 30.1-30.m according to the certification configuration request; and transmit an analyzer certification update for each of the selected system certification(s) 30.1-30.m to the corresponding POC analyzer(s) 10.1-10.n.

The above steps by the server 50 can now be described in greater detail. On one hand, the server 50 can be configured to update the selected system certification(s) 30.1-30.m within the server 50 according to the certification configuration request. On the other hand, in order to ensure that the certification configuration command (as a complete workflow) can be implemented not only on the server 50 but across the POC testing system 1, the server 50 can be configured to transmit an analyzer update for each of the selected system certification(s) 30.1-30.m to the corresponding POC analyzer(s) 10.1-10.n.

According to some embodiments, the analyzer certification update transmitted by the server 50 to the corresponding POC analyzer(s) 10.1-10.n can comprise one or more of the following:

one or more operator identifier(s) corresponding to the identified operator(s) to be granted access the respective POC analyzer 10.1-10.n; and/or one or more operator identifier(s) corresponding to the identified operator(s) to be denied access to the respective POC analyzer 10.1-10.n; and/or one or more operator identifier(s) corresponding to the identified operator(s) to be granted limited access to the respective POC analyzer 10.1-10.n.

According to some embodiments, the steps of:

the server 50 transmitting an analyzer certification update for each of the selected system certification(s) 30.1-30.m to the corresponding POC analyzer(s) 10.1-10.n;

the one or more POC analyzer(s) 10.1-10.n receiving the analyzer certification update; and the one or more POC analyzer(s) 10.1-10.n updating their respective analyzer certification according to the analyzer certification update can be initiated by one or more POC analyzer(s) 10.1-10.n requesting an update of the corresponding system certification(s) 30.1-30.m. Correspondingly, the one or more POC analyzer(s) 10.1-10.n can be configured to request analyzer certification update(s) on occurrence(s) of certain event(s) and/or at regular intervals. According to some embodiments, the one or more POC analyzer(s) 10.1-10.n can be configured to request an analyzer certification update upon a login by an operator and/or upon startup and/or upon shutdown and/or upon docking (into a docking station) of the respective POC analyzer 10.1-10.n. This is shown on the use case diagrams with dotted lines.

To summarize the analyzer certification update(s), according to some embodiments, the analyzer certification update(s) may be implemented using "server push" technology (that is server initiated) and/or a "client pull" technology (client—in this case POC analyzer initiated). The server push implementation of analyzer certification update(s) can be advantageous for POC analyzers 10.1-10.$n$ which are continuously communicating with the server, while the client pull implementation of analyzer certification update(s) can be advantageous for POC analyzers 10.1-10.$n$ which communicate with the server only on an event basis, such as periodically and/or upon a login by an operator and/or upon startup and/or upon shutdown of the respective POC analyzer 10.1-10.$n$. Also, according to some embodiments, the POC analyzers 10.1-10.$n$ can request an analyzer certification update from the server 50 upon expiry of a validity of the respective system certification(s) 30.1-30.$m$.

Figure 9B:
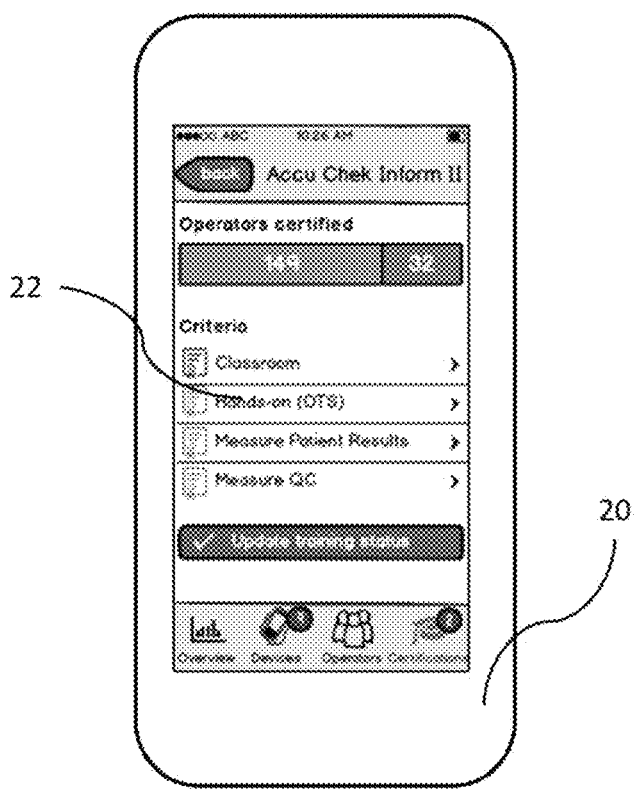
Figure 9C:
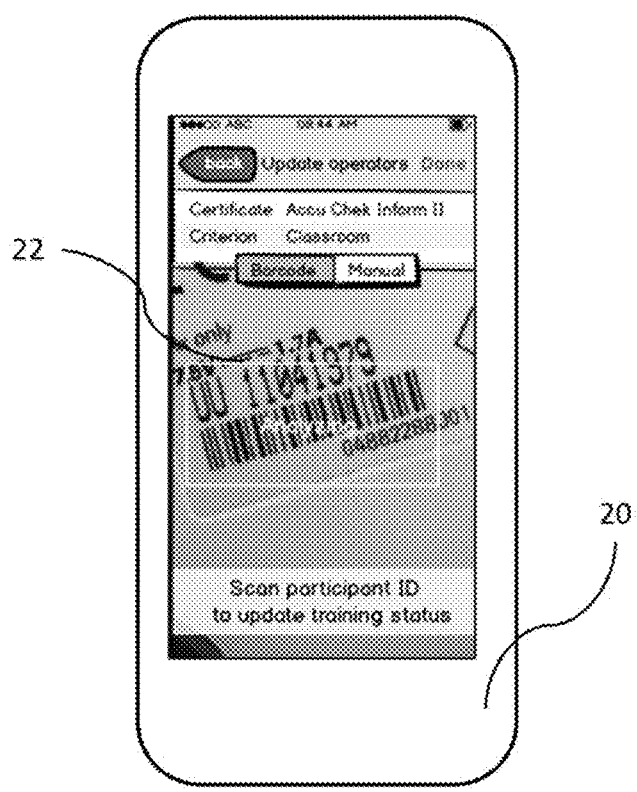
Figure 9D:
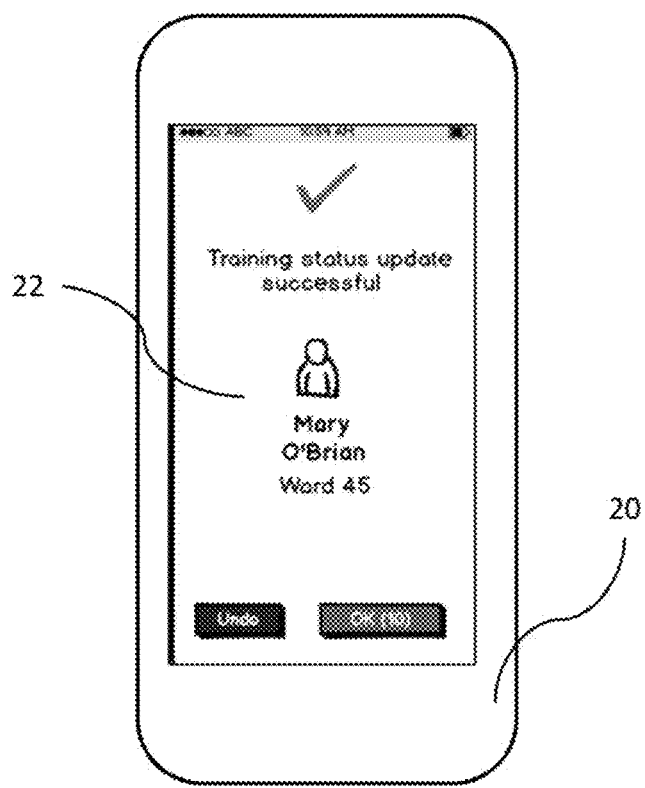

According to some embodiments, as shown in FIG. 9B, receiving the certification configuration command via the user interface 22 of the portable computing device 20 can comprise a selection of one or more certification criteria via the user interface 22. Certification criteria can comprise (but is not limited to) one or more of the following:
Classroom training;
Hands-on training;
Training on patient sample analysis;
Training on calibration and/or quality control.

In some embodiments according to which one or more certification criteria corresponding to one or more system certification(s) 30.1-30.$m$ are defined, the one or more POC analyzer(s) 10.1-10.$n$ can be configured to control access of the identified operator(s) to the respective POC analyzer 10.1-10.$n$ according to the one or more certification criteria of the selected system certification(s) 30.1-30.$m$. Such control of access can comprise allowing an operator to use only certain functions of the POC analyzer 10.1-10.$n$. For example, an operator who has the certification criterion "Training on patient sample measurement" but not the certification criterion "Training on calibration and/or quality control" may only perform patient sample analysis with the respective POC analyzer(s) 10.1-10.$n$ but not calibration and quality control.

According to some embodiments, the server 50 can be further configured to:
mark a list of authorized operators for each of the POC analyzer(s) 10.1-10.$n$ corresponding to the selected system certification(s) 30.1-30.$m$ as invalid; and/or
update a list of authorized operators for each of the POC analyzer(s) 10.1-10.$n$ corresponding to the selected system certification(s) 30.1-30.$m$ according to the analyzer certification update.

In such embodiment(s) the analyzer certification update can comprise a list of authorized operators for the respective POC analyzer(s) 10.1-10.$n$.

According to embodiments of the disclosed system/method, the POC analyzer(s) 10.1-10.$n$ can be configured to perform one or more of the following:
blood glucose testing;
coagulation testing;
blood gas or electrolytes analysis;
urinalysis;
cardiac markers analysis;
hemoglobin diagnostics;
infectious disease testing
cholesterol screening;
nucleic acid testing (NAT).

According to some embodiments, the portable computing device 20 can be one of the following:
a mobile phone, in particular a smartphone;
a tablet computer;
a laptop computer;
a dedicated PDA device.

According to some embodiments, the server 50 can be configured to:
retrieve analytical data from the one or more POC analyzer(s) 10.1-10.$n$ such as data representing the measurement of patient health parameter(s);
update program data of the one or more POC analyzer(s) 10.1-10.$n$ such as a software update.

It will be understood that not all steps of the methods herein disclosed are necessarily carried out in the listed/described order. In particular, a configuration command may be received by the portable computing device before identifying POC analyzer(s); operators may be identified before selecting a certification; analyzer update command(s) may be transmitted by the server to the POC analyzer(s) before updating system parameter(s) or a first POC analyzer may be flagged as inactive before the second (replacement) POC analyzer is updated with the analyzer parameters of the first POC analyzer.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A point of care (POC) testing system, the POC system comprising:
one or more POC analyzer(s) for analyzing one or more patient sample(s), the one or more POC analyzer(s) each having an analyzer identifier for identifying the one or more POC analyzer(s);
a portable computing device configured to identify the one or more POC analyzer(s) based on the corresponding analyzer identifier, the portable computing device having a user interface configured to receive a configuration command, wherein the configuration command received by the portable computing device comprises a relocation command corresponding to a relocation of the identified POC analyzer(s), wherein the portable computing device generates a configuration request according to the configuration command, the configuration request comprising the analyzer identifier(s) of the identified POC analyzer(s);
a server for storing system parameter(s) corresponding to the one or more POC analyzer(s), wherein the portable computing device is configured to transmit the configuration request to the server, wherein the configuration request transmitted by the portable computing device to the server comprises the relocation command, wherein the server is configured to receive the configuration request, update at least one system parameter corresponding to at least one identified POC analyzer(s), wherein the server is configured to update one or more system parameter(s) in accordance with the relocation of the identified POC analyzer(s), and transmit an analyzer update command comprising at least one analyzer parameter update to at least one identified POC analyzer(s), wherein the server is further configured to retrieve at least one analyzer parameter update in accordance with the relocation of the identified POC analyzer(s); and a communication network configured to communicatively connect the one or more POC analyzer(s) and the portable computing device with the server, wherein the one or more POC analyzer(s) are configured to receive the analyzer update command and to update at least one analyzer parameter according to the corresponding analyzer parameter update.

2. The POC testing system according to claim 1, wherein the one or more POC analyzer(s) are configured to request an analyzer update on occurrence(s) of certain event(s) and/or at regular intervals.

3. The POC testing system according to claim 1, wherein the server is configured to transmit the at least one retrieved analyzer parameter update to the identified POC analyzer(s).

4. The POC testing system according to claim 1, wherein the server is configured to store one or more system certification(s), each corresponding to one or more POC analyzer(s).

5. The POC testing system according to claim 1, wherein the server is configured to store a system certification for each type/class of POC analyzers.

6. The POC testing system according to claim 1, wherein the server is configured to store a system certification for each of the one or more POC analyzers.

7. The POC testing system according to claim 1, wherein the server is configured to retrieve analytical data from the one or more POC analyzer(s) and update program data of the one or more POC analyzer(s).

8. The POC testing system according to claim 7, wherein the analytical data is data representing the measurement of patient health parameter(s).

9. The POC testing system according to claim 7, wherein program data is a software update.

10. The POC testing system according to claim 1, wherein relocation of one or more POC analyzer(s) can comprise both physical and/or logical relocation of one or more POC analyzer(s).

11. The POC testing system according to claim 1, further comprises,
an identifier reader.

12. A method for configuration of a point of care (POC) testing system, the method comprising:
providing one or more POC analyzer(s) for analyzing one or more patient sample(s), the one or more POC analyzer(s), each having an analyzer identifier for identifying the POC analyzer(s);
providing a portable computing device;
providing a server for storing system parameter(s) corresponding to the one or more POC analyzer(s);
communicatively connecting the one or more POC analyzer(s) and the portable computing device with the server by a communication network;
identifying at least one of the one or more POC analyzer(s) based on the corresponding analyzer identifier(s) by the portable computing device;
receiving a configuration command via a user interface of the portable computing device;
generating a configuration request according to the configuration command by the portable computing device, the configuration request comprising the analyzer identifier(s) of the identified POC analyzer(s);
transmitting the configuration request to the server by the portable computing device;
receiving the configuration request by the server;
updating at least one system parameter corresponding to the identified POC analyzer(s) by the server;
transmitting an analyzer update command to the identified POC analyzer(s) by the server, the analyzer update command comprising at least one analyzer parameter update;
receiving the respective analyzer update command by the identified POC analyzer(s);
updating of at least one analyzer parameter according to the corresponding analyzer parameter update by the identified POC analyzer(s);
receiving a relocation command corresponding to a relocation of the identified POC analyzer(s), the relocation command being comprised within the configuration command;
transmitting the relocation command to the server by the portable computing device, the relocation command being comprised within the configuration request;
updating one or more system parameter(s) in accordance with the relocation of the identified POC analyzer(s) by the server;
retrieving at least one analyzer parameter update in accordance with the relocation of the one or more POC analyzer(s) by the server; and
transmitting the retrieved analyzer parameter update(s) to the identified POC analyzer(s).

13. The method for configuration of a POC testing system according to claim 12, wherein the server transmitting an analyzer update command comprises at least one analyzer parameter update to the identified POC analyzer(s).

14. The method for configuration of a POC testing system according to claim 13, wherein the identified POC analyzer(s) receives the analyzer update command.

15. The method for configuration of a POC testing system according to claim 14, wherein the identified POC analyzer(s) updating of at least one analyzer parameter according to the corresponding analyzer parameter update is initiated by one or more POC analyzer(s) requesting an analyzer update on occurrence(s) of certain event(s) and/or at regular intervals.

16. The method for configuration of a POC testing system according to claim 15, further comprises,
retrieving analytical data from the one or more POC analyzer(s); and/or
updating of program data of the one or more POC analyzer(s).

17. A method for configuration of a point of care (POC) testing system, the method comprising:
providing one or more POC analyzer(s) for analyzing one or more patient sample(s), the one or more POC analyzer(s), each having an analyzer identifier for identifying the POC analyzer(s);
providing a portable computing device;
providing a server for storing system certification(s) corresponding to the one or more POC analyzer(s);
providing one or more operator(s) of the POC testing system with corresponding operator identifier(s);
communicatively connecting the one or more POC analyzer(s) and the portable computing device with the server by a communication network;
receiving a certification configuration command via a user interface of the portable computing device;

generating a certification configuration request according to the configuration command by the portable computing device;

transmitting the certification configuration request to the server by the portable computing device;

receiving the certification configuration request by the server;

updating the selected system certification(s) according to the certification configuration request;

transmitting an analyzer certification update for each of the selected system certification(s) to the identified POC analyzer(s) by the server;

receiving the respective analyzer certification update by the identified POC analyzer(s);

updating of analyzer certification according to the corresponding analyzer certification update by the identified POC analyzer(s).

18. The method for configuration of a POC testing system according to claim 17, wherein the configuration request comprising the analyzer identifier(s) of the identified POC analyzer(s) comprises the one or more operator(s) corresponding to the identified operator and data identifying the selected system certification(s).

19. The method for configuration of a POC testing system according to claim 17, wherein the operator identifier(s) is/are identifier tags.

20. The method for configuration of a POC testing system according to claim 19, further comprises, providing an identifier reader operator on the portable computing device to read the identifier tags.

* * * * *